United States Patent [19]
Reisinger et al.

[11] Patent Number: 6,160,156
[45] Date of Patent: Dec. 12, 2000

[54] PROCESS FOR THE PREPARATION OF OLIGOCARBONATES

[75] Inventors: Claus-Peter Reisinger; Wolfgang Ebert, both of Krefeld, Germany

[73] Assignee: Bayer Aktiengesellschaft, Leverkusen, Germany

[21] Appl. No.: 09/458,802

[22] Filed: Dec. 10, 1999

[30] Foreign Application Priority Data

Dec. 22, 1998 [DE] Germany .......................... 198 59 289

[51] Int. Cl.$^7$ .................................................. C07C 68/00
[52] U.S. Cl. .......................... 558/274; 558/271; 558/272; 558/273
[58] Field of Search ..................................... 558/274, 271, 558/272, 273

[56] References Cited

U.S. PATENT DOCUMENTS

| | | | |
|---|---|---|---|
| 4,187,242 | 2/1980 | Chalk | 260/463 |
| 5,191,001 | 3/1993 | Kuhlig et al. | 524/125 |
| 5,498,742 | 3/1996 | Buysch et al. | 558/274 |

FOREIGN PATENT DOCUMENTS 1572291  7/1980  United Kingdom .

*Primary Examiner*—Michael G. Ambrose
*Attorney, Agent, or Firm*—Joseph C. Gil; Aron Preis

[57] ABSTRACT

The invention relates to a process for the preparation of aromatic oligocarbonates from dihydroxy compounds, CO and $O_2$ in the presence of a platinum metal catalyst, a cocatalyst, a quaternary salt and a base, which is carried out in an inert organic solvent which, under the reaction conditions, forms an azeotrope with water, and this azeotrope is removed from the reaction mixture.

10 Claims, No Drawings

PROCESS FOR THE PREPARATION OF OLIGOCARBONATES

It is known in principle to prepare organic oligocarbonates by oxidative reaction of an aromatic dihydroxy compound with carbon monoxide in the presence of a noble metal catalyst (DE-OS 27 38 437); these oligocarbonates can then be subjected to condensation to give polycarbonate (DE-OS 40 32 924). Palladium is preferably employed as the noble metal. A cocatalyst (e.g. salts of manganese or cobalt), a base, a quaternary salt, various quinones or hydroquinones and drying agents are additionally employed. The process can be carried out in an inert solvent, preferably methylene chloride (DE-OS 28 15 501).

However, the efficiency of the catalyst systems described is low; the noble metal palladium is often even employed in a stoichiometric amount. The highest activity described hitherto is fewer than five catalysis cycles per palladium atom (DE-OS 28 15 501).

It has now been found, surprisingly, that the addition to the reaction mixture of inert organic solvents which form an azeotrope with water under the reaction conditions and the removal of this azeotrope from the reaction mixture enables the activity of the catalyst system to be increased considerably.

The invention thus provides a process for the preparation of an aromatic oligocarbonate of the formula

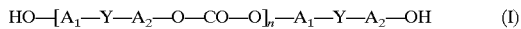

HO—[A$_1$—Y—A$_2$—O—CO—O]$_n$—A$_1$—Y—A$_2$—OH    (I)

wherein

A$_1$, A$_2$, independently of one another represent divalent, optionally branched or substituted, carbocyclic, heterocyclic or aromatic groups, Y denotes a divalent group, such as alkylene, alkylidene, cycloalkylene, cycloalkylidene, —S—, —O—, —SO$_2$—, —SO— and —CO— or a single bond and n can assume numbers from 1 to 75, by reaction of an aromatic hydroxy compound of the formula

HO—A$_1$—Y—A$_2$—OH    (II)

wherein A$_1$, A$_2$ and Y have the abovementioned meanings, with carbon monoxide and oxygen in the presence of a platinum metal catalyst, a cocatalyst, a base and optionally a quaternary salt, as well as an inert organic solvent, wherein, under the reaction conditions, the inert organic solvent forms an azeotrope with the water formed in the reaction and this azeotrope is removed from the reaction mixture.

In a preferred embodiment, the removal of the water from the reaction mixture as an azeotrope with the solvent is assisted by stripping with excess reaction gas. It is decisive here that more than 5 vol. %, preferably more than 10 vol. %, of the solvent are removed from the reaction mixture in the form of the azeotrope. Under pure stripping conditions (DE-OS 44 03 075), i.e. without azeotrope formation with the organic solvent and simultaneous removal of the azeotrope from the reaction mixture, significantly lower conversions are achieved.

The process according to the invention for oligocarbonate formation is carried out at a reaction temperature of 30 to 200° C., preferably 30 to 150° C., particularly preferably 60 to 130° C., under a total pressure of 1 to 200 bar, preferably 1 to 60 bar, particularly preferably 1 to 20 bar.

Suitably boiling halogenated hydrocarbons and aromatic solvents which form an azeotrope with water, such as chlorobenzene, dichlorobenzene, fluorobenzene, benzene, anisole, methylene chloride or 1,2-dichloroethane, and optionally also mixtures thereof, can be used as the inert organic solvent. Chlorobenzene is particularly preferably employed. The reaction mixture can comprise the inert solvent in an amount of 1–99 wt. %, preferably 20–98 wt. %, particularly preferably 40–98 wt. %.

Most of the solvent entrained during the removal of water can be separated off from the water and fed to the reflux to the reactor by a separating organ in the waste gas stream containing the azeotrope, such as e.g. a fractionating column, a distillation column with trays or packing and other apparatuses known to the expert. The separation or breaking of the azeotrope separated off can be carried out in accordance with the prior art, e.g. by extraction, freezing out or distillation.

In a preferred embodiment, the content of dissolved gases driven out with the azeotrope can be fed back to the circulating gas in the reactor after the separation. Entrained educts, solvent, products and water are separated off from the gas mixture to be recycled, which is optionally compressed before the separation, in accordance with the prior art, e.g. by adsorption, absorption or preferably by condensation. For this, the reaction gas required for the reaction, comprising carbon monoxide, oxygen and optionally an inert gas, is introduced in an amount of 1 to 10,000 Nl per liter of reaction solution, preferably 5 to 5,000 Nl per liter of reaction solution, and particularly preferably 10 to 1,000 Nl per liter of reaction solution. The gas mixture which originates from the removal of water and is to be recycled is included in the volumes mentioned in respect of its contents of CO and O$_2$.

The composition of the reaction gases carbon monoxide and oxygen can be varied within wide concentration ranges, but a CO:O$_2$ molar ratio (standardized to CO) of 1:(0.001–1.0), preferably 1:(0.01–0.5), and particularly preferably 1:(0.02–0.3) is expediently established. The oxygen partial pressure in these molar ratios is large enough to be able to achieve high space/time yields, and at the same time explosive carbon monoxide/oxygen gas mixtures are avoided. All the starting compounds may be contaminated with impurities from their preparation and storage, but in the context of the purity of the end product it is desirable to use chemicals which are as pure as possible. The reaction gases are also not subject to particular purity requirements. Thus, synthesis gas can serve as the source of CO and air as the O$_2$ carrier, but it should be ensured that no catalyst poisons, such as e.g. sulfur or compounds thereof, are introduced. In the preferred embodiment of the process according to the invention, pure CO and pure oxygen are used.

The aromatic dihydroxy compounds which can be reacted according to the invention can be substituted by C$_1$–C$_4$-alkyl, C$_1$–C$_4$-alkoxy, fluorine, chlorine or bromine. The aromatic dihydroxy compounds which can be reacted according to the invention are, for example, bis-(hydroxyphenyl)-alkanes, bis-(hydroxyphenyl)-cycloalkanes, bis-(hydroxyphenyl) sulfides, bis-(hydroxyphenyl) ethers, bis-(hydroxyphenyl) ketones, bis-(hydroxyphenyl) sulfones, bis-(hydroxyphenyl) sulfoxides, α,α'-bis(hydroxyphenyl)-diisopropylbenzenes and compounds thereof which are alkylated on the nucleus or halogenated on the nucleus.

Preferred diphenols are e.g. 2,2-bis-(4-hydroxyphenyl)-propane (bisphenol A), 2,4-bis-(4-hydroxyphenyl)-2-methylbutane, 1,3-bis-(4-hydroxycumyl)-benzene, 1,4-bis (4-hydroxycumyl)-benzene, 2,2-bis-(3-methyl-4-hydroxyphenyl)-propane, 2,2-bis-(3-chloro-4-hydroxyphenyl)-propane, bis-(3,5-dimethyl-4-hydroxyphenyl)-methane, 2,2-bis-(3,5-dimethyl-4-hydroxyphenyl)-propane, bis-(3,5-dimethyl-4-hydroxyphenyl) sulfone, 1,3-bis-(3,5-dimethyl-3-hydroxycumyl)-benzene, 1,4-bis-(3,5-dimethyl-4-hydroxycumyl)-benzene, 1,1-bis-(3,5-dimethyl-4-hydroxyphenyl)-2-methylbutane, 2,2-bis-(3,5-dichloro-4-hydroxyphenyl)-propane, 2,2-bis-(3,5-dibromo-4-hydroxyphenyl)-propane, 1,1-bis-(4-hydroxyphenyl)-cyclohexane, 1,1-bis-(4-hydroxyphenyl)-1-phenylethane and 1,1-bis-(4-hydroxyphenyl)-3,3,5-trimethylcyclohexane. Particularly preferred diphenols are 4,4'-dihydroxydiphenyl, 4,4'-dihydroxydiphenyl sulfide, 2,2-bis-(4-hydroxyphenyl)-propane, 2,2-bis-(3,5-dimethyl-4-hydroxyphenyl)-propane, 2,2-bis-(3,5-dichloro-4-hydroxyphenyl)-propane, 2,2-bis-(3,5-dibromo-4-hydroxyphenyl)-propane, 1,1-bis-(4hydroxyphenyl)-1-phenylethane, 1,1-bis-(4-hydroxyphenyl)-cyclohexane and 1,1-bis-(4-hydroxyphenyl)-3,3,5-trimethylcyclohexane.

The oligocarbonates can be branched by employing small amounts of branching agents. Examples of suitable branching agents are phloroglucinol, 4,6-dimethyl-2,4,6-tri-(4-hydroxyphenyl)-hept-2-ene, 4,6-dimethyl-2,4,6-tri-(4-hydroxyphenyl)heptane, 1,3,5-tri-(4-hydroxyphenyl)-benzene, 1,1,1-tri-(4-hydroxyphenyl)-ethane, tri-(4-hydroxy-phenyl)-phenylmethane, 2,2-bis-(4,4-bis-(4-hydroxyphenyl)-cyclohexyl)-propane, 2,4-bis-(4-hydroxyphenyl-isopropyl)-phenol, 2,6-bis-(2-hydroxy-5'-methyl-benzyl)-4-methylphenol, 2-(4-hydroxyphenyl)-2-(2,4-dihydroxyphenyl)-propane, hexa-(4-(4-hydroxyphenyl-isopropyl)-phenyl)-orthoterephthalic acid ester, tetra-(4-hydroxyphenyl)-methane, tetra-(4-(4-hydroxyphenyl-isopropyl)-phenoxy)-methane, 1,1-bis-((4',4"-dihydroxytriphenyl)-methyl)-benzene and in particular α,α', α"-tris-(4-hydroxy-phenyl)-1,3,5-triisopropenylbenzene.

The 0.05 to 2 mol % of branching agents, based on the moles of diphenol employed, optionally to be co-used can be either initially introduced with the diphenols themselves in the organic solvent or added during the reaction.

Bases which can be employed in the process according to the invention are alkali metal hydroxides, alkali metal salts and quaternary salts of weak acids, such as alkali metal tert-butylates. The mono- or di-alkali metal salt or the quaternary salts of the aromatic dihydroxy compounds of the general formula (II) which is to be converted into the organic oligocarbonate can also be used. The alkali metal salts can be lithium, sodium, potassium, rubidium or caesium salts and the quaternary salts can be, inter alia, tetraalkylammonium or tetraalkylphosphonium salts. Preferably, mono- and dilithium, mono- and disodium and mono- and dipotassium diphenolates or lithium tert-butylate, sodium tert-butylate or potassium tert-butylate are employed, particularly preferably the mono- or dipotassium diphenolate of the aromatic dihydroxy compound of the general formula (II) and potassium tert-butylate.

The base is added in catalytic amounts. The ratio of platinum metal, e.g. palladium, to base is preferably chosen such that 0.1 to 500, preferably 0.3 to 200, particularly preferably 0.9 to 130 equivalents of base are employed per gram atom of platinum metal, e.g. palladium.

The platinum metal catalysts suitable for the process according to the invention comprise at least one noble metal of group VIII, preferably palladium. It can be added in various forms in the process according to the invention. Palladium can be employed in the metallic form or, preferably, in the form of palladium compounds of oxidation levels 0 and +2, such as, for example, palladium(II) acetylacetonate, halides, carboxylates of $C_2$–$C_{18}$-carboxylic acids, nitrates or oxides or palladium complexes, which can contain, for example, olefins, amines, phosphorus compounds and halides. Palladium bromide and palladium acetylacetonate are particularly preferred.

The amount of platinum metal catalyst is not limited in the process according to the invention. Preferably, the catalyst is added in an amount such that the concentration of the metal in the reaction mixture is 1–3,000 ppm, and concentrations of 5–500 ppm are particularly preferred.

A metal of groups III A, III B, IV A, IV B, V B, I B, II B, VI B or VII B, of the rare earth metals (atomic numbers 58–71) or of the iron group of the periodic table of the elements (Mendeleev), and optionally also mixtures thereof, is used as the cocatalyst for the process according to the invention, it being possible for the metal to be employed in various oxidation levels. Mn, Cu, Co, V, Zn, Ce and Mo are preferably employed. Without limiting the process according to the invention, there may be mentioned manganese(II), manganese(III), copper(I), copper(II), cobalt(II), cobalt(III), vanadium(III) and vanadium(IV). The metals can be employed, for example, as halides, oxides, carboxylates of $C_2$–$C_6$-carboxylic acids, diketonates or nitrates, and as complex compounds, which can contain, for example, carbon monoxide, olefins, amines, phosphorus compounds and halides. Mn, Cu, Mo and Ce are particularly preferably employed. Manganese compounds are especially preferably used in the process according to the invention, particularly preferably manganese(II) and manganese(III) complexes, especially preferably manganese(II) acetylacetonate and manganese(III) acetylacetonate.

The cocatalyst, which can also be formed in situ, is added in an amount such that its concentration is in the range from 0.0001 to 20 wt. % of the reaction mixture, and the concentration range is preferably from 0.005 to 5 wt. %, particularly preferably 0.01 to 2 wt. %.

The quaternary salts employed in the context of the present invention can be, for example, ammonium, guanidinium, phosphonium or sulfonium salts substituted by organic radicals, and optionally also mixtures thereof. Salts which are suitable for use in the process according to the invention are ammonium, guanidinium, phosphonium and sulfonium salts which carry, as organic radicals, $C_6$- to $C_{10}$-aryl, $C_7$- to $C_{12}$-aralkyl and/or $C_1$- to $C_{20}$-alkyl radicals and as the anion a halide, tetrafluoroborate or hexafluorophosphate. Ammonium and phosphonium salts which carry as organic-radicals $C_6$- to $C_{10}$-aryl, $C_7$ to $C_{12}$-aralkyl and/or $C_1$- to $C_{20}$-alkyl radicals and as the anion a halide are preferably employed in the process according to the invention, and tetrabutylammonium bromide and tetrabutylphosphonium bromide are particularly preferred. The amount of such a quaternary salt can be, for example, 0.1–20 wt. %, based on the weight of the reaction mixture. This amount is preferably 0.5–15 wt. %, particularly preferably 1–5 wt. %.

If a base, such as tetrabutylammonium tert-butylate, which contains a quaternary cation is used, the amount of quaternary salt, such as tetrabutylammonium bromide, added can be reduced accordingly. Optionally, the total amount of the anion of the quaternary salt added can also be compensated by other salts of this anion, such as potassium bromide.

In another embodiment, instead of the homogeneous catalyst system, heterogeneous catalysts in which the platinum metal or the platinum metal and the cocatalyst are applied to a heterogeneous support, are employed as powders or shaped bodies. The other components of the catalyst system, such as the base, the quaternary compound and optionally the cocatalyst, are furthermore dissolved homogeneously in the reaction solution. The amount of platinum metal in the total weight of the heterogeneous catalyst is 0.01 to 15 wt. %, preferably 0.05 to 10 wt. %, calculated as platinum metal.

At least one metal compound of the abovementioned type is employed as the cocatalysts on the catalyst support.

The amount of cocatalyst in the total weight of the heterogeneous catalyst is 0.01 to 15 wt. %, preferably 0.05 to 10 wt. %, calculated as the metal.

Suitable catalyst supports are one or more metal oxides from the group consisting of V, Mn, Ti, Cu, Zr, La and the rare earth metals (atomic numbers 58–71), both in the sense of chemically uniform pure substances and in a mixture, as well as iron oxides and cobalt oxides, nickel oxide, aluminium oxide, silicon oxide and magnesium oxide, zeolites and active charcoals. If the supported catalyst is employed as a powder, for mixing of the reaction components the stirred tanks to be used are equipped with stirrers which can be used for this or constructed as a bubble column reactor.

If supported catalyst powders are used as a suspension in stirred vessels or bubble columns, amounts of 0.001 to 50 wt. %, preferably 0.01 to 20 wt. %, particularly preferably 0.1 to 10 wt. % of supported catalyst powder, based on the amount of aromatic hydroxy compound employed, are used.

In preferred embodiments, the heterogeneous supported catalyst is employed in a fixed position in stirred tanks, a bubble column, a trickle phase reactor or cascades of these reactors. Removal of the supported catalyst is then omitted completely.

Suitable reactors for the process according to the invention with a homogeneous or heterogeneous catalyst are stirred tanks, autoclaves and bubble columns, it being possible for these to be employed as individual reactors or as a cascade. In a cascade, 2 to 15, preferably 2 to 10, particularly preferably 2 to 5 reactors can be connected in series.

For mixing the reaction components, the stirred tanks to be used according to the invention are equipped with stirrers which are suitable for this. Such stirrers are known to the expert. Examples which may be mentioned are: disc, impeller, propeller, paddle, MIG and Intermig stirrers, tube stirrers and various types of hollow stirrers. Preferred stirrers are those which allow effective mixing of gases and liquids, for example hollow tube gassing stirrers, propeller stirrers etc.

Bubble columns which can be employed in the process according to the invention are the following types: simple bubble columns, bubble columns with inserts, such as e.g.: bubble columns with parallel chambers, cascade bubble columns with sieve trays or single-hole trays, bubble columns with packings, with static mixers, pulsed sieve tray bubble columns, loop reactors, such as e.g.: mammoth loop reactors, downwards-flow loop reactors, jet loop reactors, free jet reactors, jet nozzle reactors, bubble columns with liquid-immersed jets, downwards-flow/upwards-flow bubble columns and other bubble column reactors known to the expert (Chem. Ing. Tech. 51 (1979) no. 3, p. 208–216; W.-D. Deckwer, Reaktionstechnik in Blasensäulen, [Reaction Techniques in Bubble Columns], Otto Salle Verlag 1985).

In a preferred embodiment, bubble column reactors and bubble column cascades which allow effective mixing of gas and liquids, such as, for example, cascade bubble columns and loop reactors, are employed. Distributing and redispersing organs can be located along the longitudinal axis of the bubble column reactors to maintain good thorough mixing of the liquid and reaction gas. Fixed redispersing organs which are employed are single-hole trays, perforated plates, sieve trays and other inserts known to the expert. For the initial dispersion of the reaction gas in the liquid phase during metering in, conventional devices, such as porous sinter plates, perforated plates, sieve trays, push-in tubes, nozzles, gassing rings and other dispersing devices known to the expert can be employed.

The process according to the invention can be carried out in various procedure variants. One possibility is the discontinuous procedure. In this, CO and oxygen are passed into the reaction mixture either through a gassing stirrer, as in the case of a stirred tank, or through other known gas distribution organs. When the optimum conversion has been reached, the reaction mixture is removed from the reactor or optionally worked up in the reactor. In the case where pulverulent supported catalysts are used, these can be separated off from the reaction mixture e.g. by filtration, sedimentation or centrifugation.

Supported catalysts used in discontinuous experiments can optionally be employed repeatedly without purification for the same starting substances. In the case of a continuous procedure, the supported catalysts employed can remain in the reactor for a long time and can optionally be regenerated.

Preferably, a continuous procedure in an individual reactor or in a cascade of several reactors is employed. If heterogeneous catalysts in a fixed position are used, these can remain in the reactor for a long time and can also optionally be regenerated there.

EXAMPLES

Example 1

0.3 mmol palladium bromide, 3.0 mmol manganese(II) acetylacetonate and 30.0 mmol tetrabutylammonium bromide in 350 mol chlorobenzene were initially introduced into a 600 ml pot with a ground lid and with a heating jacket, gassing stirrer, condenser and subsequent cold trap, and carbon monoxide (3 l/h) was passed through at 80° C. for one hour to dissolve the catalyst. 21.0 g bisphenol A and 5.2 mmol potassium tert-butylate were then added, the mixture was heated to 80° C. and, by introducing 180 Nl/h of a gas mixture of carbon monoxide and oxygen (95:5 vol. %) under normal pressure, the reaction was started. After a reaction time of 6 h, in each case 0.8 g bisphenol A per hour was added as a solid in the course of 8 hours. After a total of 20 h, 95% of the total amount of bisphenol A had reacted, according to analysis by HPLC. The product spectrum contained the oligomers according to structure (I) where n=1–7. The cold trap contained approx. 10–15% of the amount of chlorobenzene employed; the phase separation which always occurs allows easy removal of the water formed from the condensate. After the end of the experiment, the reaction mixture had a residual water content of less than 250 ppm.

Example 2

0.15 mmol palladium bromide, 11 mmol tetrabutylammonium bromide and 8 g bisphenol A in 90 ml chlorobenzene were initially introduced into a 250 ml autoclave with a gassing stirrer, condenser and subsequent cold trap and were dissolved by introducing carbon monoxide (3 l/h) at 90° C. for 30 min. 1.1 mmol manganese(III) acetylacetamide and 5.2 ml potassium tert-butylate with 10 ml chlorobenzene were then added and, by introducing 80 Nl/h of a gas mixture of carbon monoxide and oxygen (95:5 vol. %) under a total pressure of 3 bar at 110° C., the reaction was started. After 6 h, the reaction solution was diluted with 100 ml methylene chloride. HPLC analyses showed that a total of 91% of the bisphenol A had reacted and the product spectrum contained the oligomers according to structure (I) where n=1–9. 12 g of a chlorobenzene/water suspension were condensed in the cold trap. After the end of the experiment, the reaction mixture had a residual water content of less than 250 ppm.

Example 3 (comparison)

0.15 mmol palladium bromide, 11 mmol tetrabutylammonium bromide and 8 g bisphenol A in 90 ml chlorobenzene were initially introduced into a 250 ml autoclave with a gassing stirrer, condenser and subsequent cold trap and were dissolved by introducing carbon monoxide (3 l/h) at 90° C. for 30 min. 1.1 mmol manganese(III) acetylacetonate and 5.2 mmol potassium tert-butylate with 10 ml chlorobenzene were then added and, by introducing 80 Nl/h of a gas mixture of carbon monoxide and oxygen (95:5 vol. %) under a total pressure of 7 bar at 110° C., the reaction was started. After 6 h, the reaction solution was diluted with 100 ml methylene chloride. HPLC analyses showed that a total of 38% of the total amount of bisphenol A had reacted and the product spectrum contained the oligomers according to structure (I) where n=1–5. Less than 3 g of water were condensed in the cold trap. After the end of the experiment the reaction mixture had a residual water content of more than 600 ppm. The pressure and temperature setting used corresponded to pure stripping conditions, since the azeotrope was removed hardly at all from the reaction mixture. Direct comparison with example 1 demonstrates the efficiency of the removal of the azeotrope from the reaction mixture.

What is claimed is:

1. Process for the preparation of an aromatic oligocarbonate of the formula

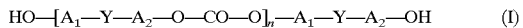  (I)

wherein $A_1$, $A_2$ independently of one another represent divalent carbocyclic or heterocyclic aromatic groups, Y denotes a divalent group, such as alkylene, alkylidene, cycloalkylene, cycloalkylidene, —S—, —O—, —SO$_2$—, —SO— and —CO— or a single bond and n can assume numbers from 1 to 75, by reaction of an aromatic hydroxy compound of the formula

  (II), wherein $A_1$, $A_2$ and Y have the abovementioned meanings, with carbon monoxide and oxygen in the presence of a platinum metal catalyst, a cocatalyst, a base and optionally a quaternary salt, as well as an inert organic solvent, wherein, under the reaction conditions, the inert organic solvent forms an azeotrope with the water formed during the reaction, and this azeotrope is removed from the reaction mixture.

2. Process according to claim 1, in which the removal of the azeotrope from the reaction mixture is assisted by excess reaction gas.

3. Process according to claim 1, in which aromatic solvents are employed as the inert organic solvent.

4. Process according to claim 3, in which chlorobenzene is employed as the inert organic solvent.

5. Process according to claim 1, in which halogenated hydrocarbons are employed as the inert organic solvent.

6. Process according to claim 5, in which 1,2-dichloroethane is used as the solvent.

7. Process according to claim 1, in which alkali metal salts or quaternary salts of weak acids are used as the bases.

8. Process according to claim 7, in which the mono- or the dialkali metal salt of the diphenol of the general formula (II) employed or a mixture thereof is used as the base.

9. Process according to claim 7, in which potassium tert-butylate is used as the base.

10. Process according to claim 1, in which alkali metal hydroxide are used as the bases.

* * * * *